(12) United States Patent
Sonbul (10) Patent No.: US 6,897,071 B2
(45) Date of Patent: May 24, 2005

(54) TOPOLOGICAL NEAR INFRARED ANALYSIS MODELING OF PETROLEUM REFINERY PRODUCTS

(75) Inventor: Yaser R. Sonbul, Damman (SA)

(73) Assignee: Saudi Arabian Oil Company, Dhahran (SA)

( * ) Notice: Subject to any disclaimer, the term of this patent is extended or adjusted under 35 U.S.C. 154(b) by 227 days.

(21) Appl. No.: 10/218,845

(22) Filed: Aug. 13, 2002

(65) Prior Publication Data

US 2004/0033617 A1 Feb. 19, 2004

(51) Int. Cl.$^7$ ............................................. G01N 21/62
(52) U.S. Cl. ............................. 436/171; 28/29; 28/164
(58) Field of Search ........................... 438/28, 29, 164, 438/171

(56) References Cited

U.S. PATENT DOCUMENTS

| | | | |
|---|---|---|---|
| 5,223,714 A | 6/1993 | Maggard | 250/343 |
| 5,360,972 A | 11/1994 | DiFoggio et al. | 250/339.12 |
| 5,397,899 A | 3/1995 | DiFoggio et al. | 250/339.09 |
| 5,446,681 A | 8/1995 | Gethner et al. | 364/554 |
| 5,475,612 A | 12/1995 | Espinosa et al. | 364/599 |
| 5,606,164 A | 2/1997 | Price et al. | 250/339.09 |
| 5,668,374 A | 9/1997 | DeFoggio et al. | 250/339.12 |
| 5,712,797 A | 1/1998 | Descales et al. | 364/499 |
| 5,861,228 A | 1/1999 | Descales et al. | 436/171 |
| 6,012,019 A | 1/2000 | Saby | 702/32 |
| 6,070,128 A | 5/2000 | Descales et al. | 702/30 |
| 6,159,255 A | 12/2000 | Perkins | 44/300 |
| 6,223,133 B1 | 4/2001 | Brown | 702/85 |

OTHER PUBLICATIONS

"TOPNIR4. A revolution in process control", created on–line Jul. 15, 2002; from Google: TopNIR.*

Barsamian "Getting the most out of your NIR analyzers", Oct. 2001; http://www.r–t–o–l.com/modules.php?name=News&file=article&sid=147.*

Lambert et al. "TOPNIR systems for online optimization of petrochemical and refining processes", Proceedings of the World Petroleum Congress (1998), 15th(vol. 2), 791–796, (Abstract).*

TECHNIP/ASE/Aug. 2000 discloses "In–line Quality Management: TOPNIR Technology"http://www.technip.com/francais/pdf/TOPNIR.pdf.*

Caroline Baeza, "TOPNIR Application—What is TOPNIR? Use TopNIR Technology to optimise Plant Operations", ABB AAT Industries, dated Aug. 4, 2002, 11 pages.

* cited by examiner

Primary Examiner—Yelena G. Gakh
(74) Attorney, Agent, or Firm—Abelman, Frayne & Schwab (57) ABSTRACT

A method of analyzing a substance exhibiting absorption in the near infrared (NIR) region subjects the substance to NIR spectroscopy, processes the data using a partial least squares (PLS) technique and identifies a component of the substance by performing a topological near infrared (TOPNIR) analysis on the processed data.

19 Claims, 8 Drawing Sheets

TOPOLOGICAL NEAR INFRARED ANALYSIS MODELING OF PETROLEUM REFINERY PRODUCTS

BACKGROUND OF THE INVENTION

Timely information on the quality of feedstocks, process streams and products is crucial in many areas of the oil products and chemicals business, and the need to obtain more information from a given chemical sample has become more acute over the past decade. To this end, analytical chemistry has been transformed into a branch of chemistry with considerable overlap with other areas of science such as physics, mathematics, computer science and Artificial Intelligence science, so that the efficiency and speed of data extraction has increased many times. The term Chemometrics is used to refer to such computerized mathematical methods and interpretation of chemical data. Statistical analysis plays a central role in Chemometrics, and the main aim is to recognize a pattern in the chemical data generated from spectral analysis instruments.

Unfortunately, many physical test methods are still time consuming and are often performed solely in a quality control laboratory, with the result that the test procedures are not accessible for plant operations. To provide more timely results, Near-Infrared (NIR) analysis, using Chemometrics database construction techniques, was introduced in the industry to predict the physical properties and chemical composition of the products. The NIR technique offers enormous potential savings for refiners in monitoring, controlling and optimizing processes. A single NIR can substitute for many traditional analyzers and provide accurate and fast results on physical and chemical properties of process streams and refined products.

Figure 1:
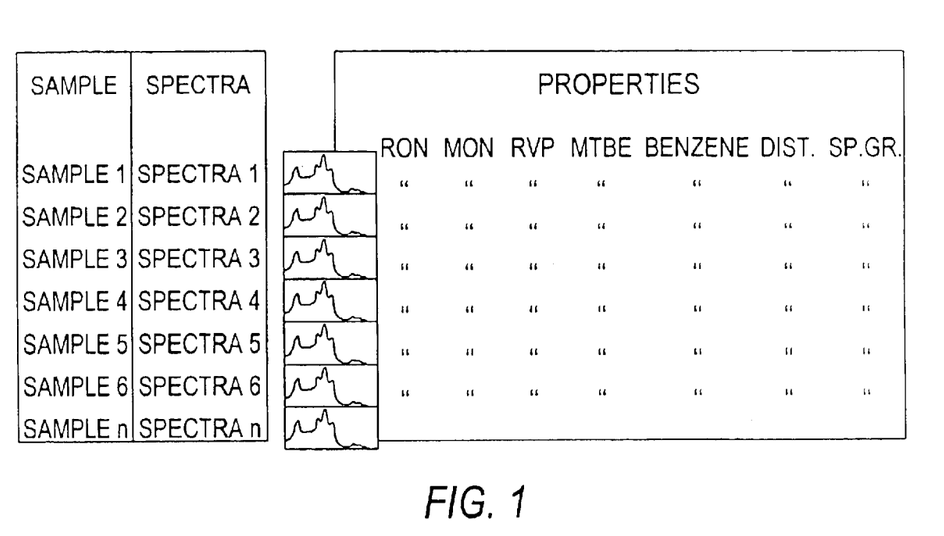
FIG. 1 is a schematic illustration of the creation of a Chemometrics database.

In order to use NIR, the chemical constituents and physical phenomena of interest must have direct or indirect absorbance in the NIR region. The time-consuming part of NIR work is the data analysis and modeling phase, where most of the work is done to find the correlation between NIR spectral characteristics and the property, or properties, of interest as measured by more traditional methods. The selected spectrum absorbencies on each sample and the correlated reference lab measurements are utilized as the databases in constructing the Chemometrics models (training-set samples). FIG. 1 is a schematic illustration of the creation of such a database.

So far, two separate NIR Chemometrics approaches have been developed for use in nearly every refinery for providing reliable quality control. These are known as PLSNIR (Partial Least Squares NIR) and TOPNIR (Topological NIR). These models allow prediction of the properties of unknown samples directly from their spectra. It must be emphasized that the reliability, accuracy and precision of properly calibrated and maintained NIR process analyzers are essential for the success of NIR as a closed-loop, feed-forward control system for on-stream performance.

Currently the TOPNIR and PLS modeling techniques, using measured NIR spectra of hydrocarbon streams, are capable of accurately predicting the following fuel, compositional and physical properties for comparison against ASTM approved methods:

RON (Research Octane Number)
MON (Motor Octane Number)
RVP (Reid Vapor Pressure)
Density
Distillation Cut Points (IBP, 5%, 10%, 20%, 30% . . . 95%, FBP)
Vapor over Liquid Ratio
Cloud Point
Flash Point
Freezing Point
Cetane Number
CFPP (Cold Filter Plugging Point)
PIONA (Paraffins, Iso-paraffins, Naphthenes, Aromatics)
% Benzene
% MTBE
% Tolune
% Xylenes These two Chemometrics modeling approaches each have their own methodology, advantages and disadvantages, and the relative accuracy of the TOPNIR and PLSNIR model predictions as a function of wavelength range and spectral resolution can be assessed using the same database.

SUMMARY OF THE INVENTION

The method in accordance with the present invention integrates the use of the TOPNIR and PLS techniques into one Chemometrics approach. In this method, PLS is used for the first time in treating the TOPNIR database.

In one aspect of the present invention, PLS is used to highlight the outliers of the TOPNIR database in a systematic order and then to recorrect a bad test result and avoid wasting the whole set of sample results in the database.

In another aspect of the present invention, PLS is used for suggesting an excellent corrected lab test result on the bad given value.

In a further aspect of the present invention, PLS is used to improve the results of the TOPNIR densification process. In the method accordance with the present invention, PLS is used to indicate a wrong densification direction and show where the error is enlarged. All mistaken artificial samples can then be removed from the database and bad real samples may be reedited with good PLS predicted values. Thereafter, the densification process can be repeated with an enhanced level of confidence. This step maintains a balanced equation of the model robustness and accuracy.

In a further development of this aspect, PLS is used in the method in accordance with the present invention to highlight affected good samples that have been turned bad by misuse of the densification process and prevent the deletion of good samples that should be kept.

Thus, in one embodiment, the present invention is directed to a method of analyzing a substance exhibiting absorption in the near infrared (NIR) region, comprising a data obtaining step of obtaining a first data set of NIR spectroscopic data samples by subjecting the substance to NIR spectroscopy, a generating step of generating a second data set of NIR spectroscopic data samples by processing the first data set using a partial least squares (PLS) technique, and an identifying step of identifying a component of the substance by performing a topological near infrared (TOPNIR) analysis on the second data set.

In another embodiment, the present invention is directed to a method of analyzing a substance exhibiting absorption in the near infrared (NIR) region, comprising a data obtaining step of obtaining a first data set of NIR spectroscopic data samples by subjecting the substance to NIR spectroscopy, an analysis step of performing a first topological near infrared (TOPNIR) analysis on the first data set to generate a second data set of NIR spectroscopic data samples, a generating step of generating a third data set of NIR spectroscopic data samples by processing the second data set using a partial least squares (PLS) technique, and an identifying step of identifying a component of the substance by performing a second TOPNIR analysis on the third data set.

BRIEF DESCRIPTION OF THE DRAWINGS

FIG. 11 is a table for comparing results of conventional PLS and TOPNIR models.

FIG. 12 is a table for comparing results of the conventional TOPNIR method and the PLS enhanced TOPNIR method in accordance with the present invention.

DETAILED DESCRIPTION OF THE PREFERRED EMBODIMENTS

To aid understanding of the description of the preferred embodiments, the following key words are now defined.

Partial Least Squares (PLS): PLS is a statistical method and an effective Chemometrics approach for constructing predictive models that was developed in the 1960's by Herman Wold. It has been applied in monitoring and controlling industrial processes. PLS is described in more detail below.

Figure 2:
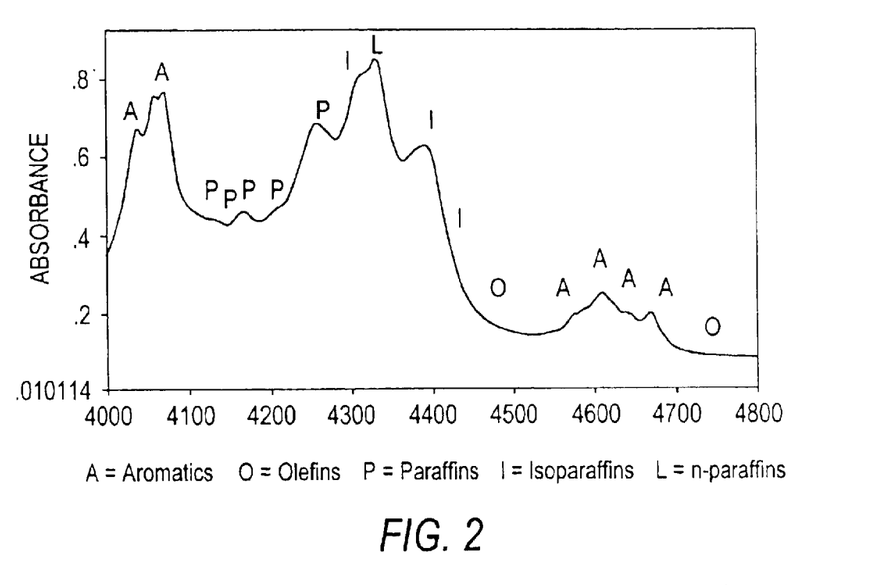
FIG. 2 is a typical NIR spectrum.

NIR Spectrum: A NIR spectrum is obtained from the absorbency measurements from an NIR analyzer, typically as SPC files. TOPNIR and PLS models each have a wavelength range of 4000–4800 nm. A typical NIR spectrum is shown in FIG. 2.

Outlier: An outlier is a data point that falls well outside of the main population. Outliers result from lab measurement errors, samples from different categories and instrument error. It is important to check for and remove outliers in both the training set and the set of unknowns that the calibration is to be tested on.

Calibration Modeling: The process of constructing a model that is used to predict characteristics or properties of unknown samples. The model is constructed from a calibration data set with measured multivariate responses and corresponding known sample concentrations or physical characteristics of interest.

Cross Validation: A process used to validate models whereby the calibration set is divided into calibration and validation subsets. A model is built with the calibration subset and is used to predict the validation subset. This process is repeated using different subsets until every sample has been included in one validation subset. The predicted results are then used to validate the performance of the model.

Figure 3:
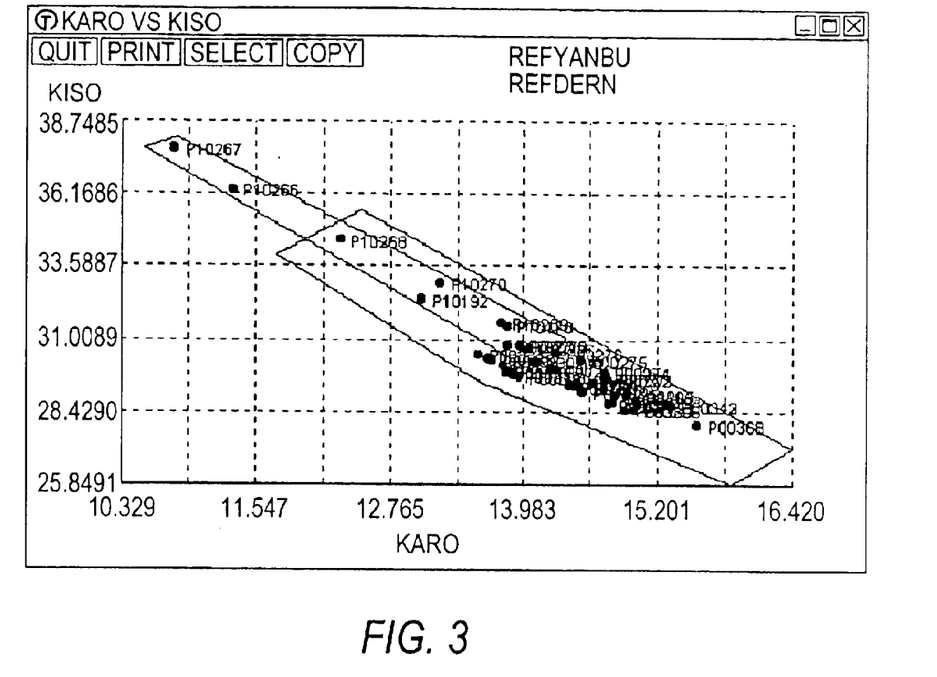
FIG. 3 is an illustration of data before densification.
Figure 4:
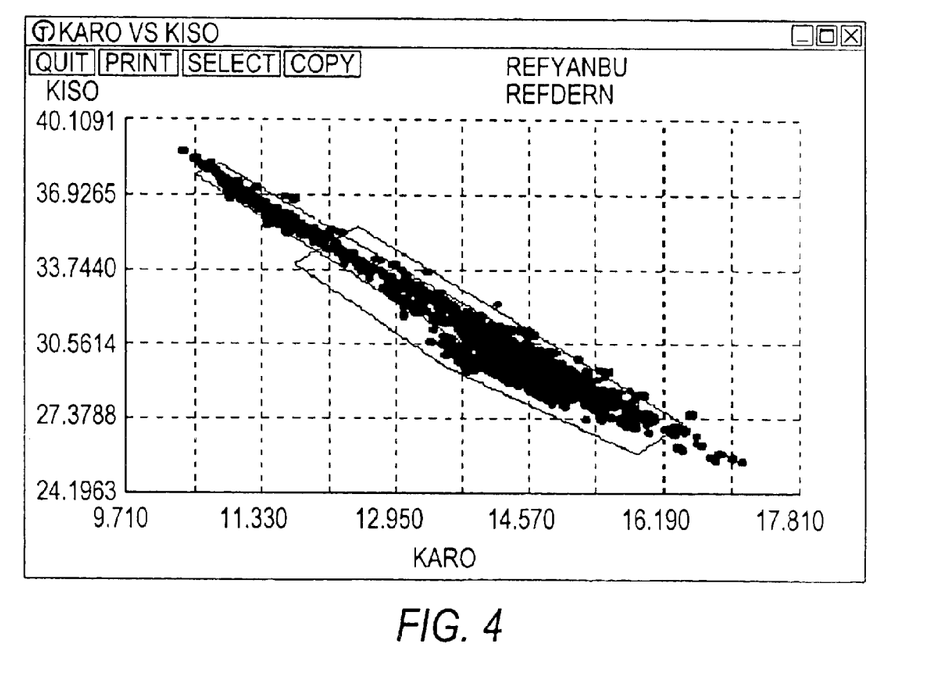
FIG. 4 is an illustration of the data of FIG. 3 after densification.

Densification: Densification is a process used by TOPNIR to improve the robustness of a model—from the typically 30 samples per stream provided by the production plant to hundreds of additional reference samples based on the TOPNIR sample library. By increasing the number of samples, TOPNIR is able to make predictions across the whole of the operating envelope. Because it performs densification during configuration and during the prediction calculation, the TOPNIR model is robust and can deal with inliers and outliers. FIGS. 3 and 4 show how artificial samples are added using an aggregate plane to display the data before (FIG. 3) and after (FIG. 4) densification.

Aggregates: An NIR spectrum may characterize the sample, but the quantity of data is enormous. Even with 42 bands of wavelength, comparing samples is very difficult. Therefore aggregates are calculations based on the absorbencies at a selection of wavelengths that characterize some property of the process stream, e.g., Karo=W4060*W4670/W4332/W4485*7.3+5. The calculation for aggregates is defined during configuration of the TOPNIR model based upon experience of previous models that have worked successfully. The aggregates are used to differentiate products but are not used during the prediction process itself. Therefore, neighbors used during a prediction may not be neighbors on one or all spectral planes.

Operating Envelope: At any point in time a process stream is characterized by a range of components that can be measured either by laboratory analysis or predicted from NIR spectra. A process stream changes for a variety of operating reasons, which may include the base stock, the operating severity of the processing units and the catalyst activity. The variation of all these factors can be seen as the operating envelope for the production process.

The well known PLS method creates a simplified representation of the spectroscopic data by a process known as spectral decomposition. The PLS algorithm then calculates the concentration, or property value, weighted average spectrum of all the spectra of the fuels in the calibration matrix. This calculation is followed by a computationally intensive procedure, accomplished by performing outlier detection and removal, and then applying cross-validation calculations for all samples in the training set.

In the cross-validation procedure, a given number of samples, which in the tests set forth below is one, are removed from the calibration data set, and a calibration model calculated from the remaining samples in the training set is used to predict the concentration (property value) of the removed samples. The residual errors, or the differences between the predicted and known concentration values, are squared and summed to determine the predicted error. Repeating this cross-validation process for the other samples in the training set results in a redefined regression model useful in predicting the properties of unknown fuels. The results of spectral decomposition give one set of scores and one set of factors (loading vectors) for calibration for each component of interest.

After a calibration model is established, it has to be tested by validation experiments, in which the calibration is applied to similar fuels that were not part of the training set. The predicted property values may then be compared with those derived by established ASTM procedures. It is critical to establish the correct number of factors to be used in the correlation files, as the predicted fuel property values calculated from the model depends on how many factors are used in the model. Too few factors will not adequately model the system, while too many factors will introduce noise vectors in the calibration which will result in less than optimum prediction for samples outside the calibration set.

Figure 5:
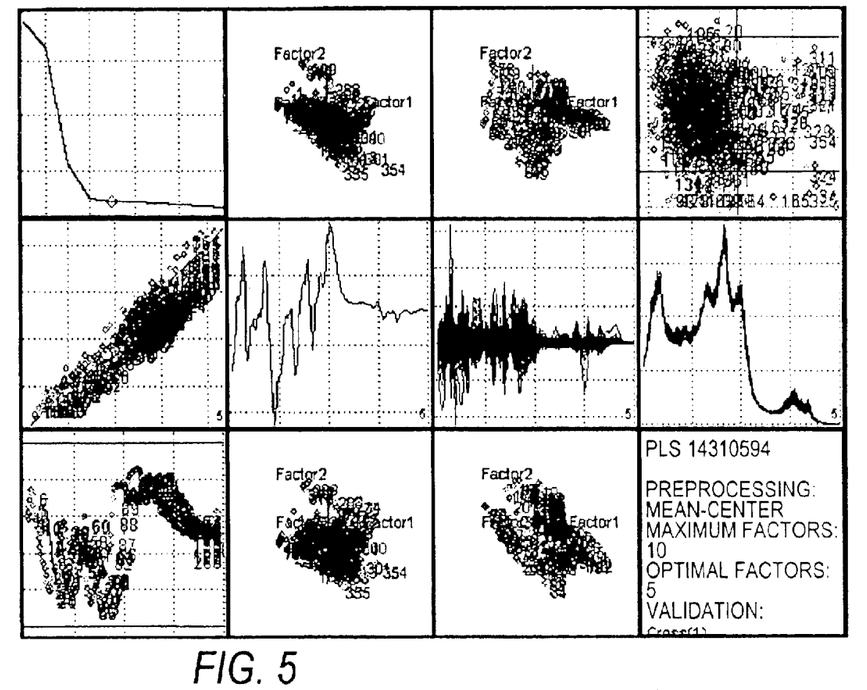
FIG. 5 is an illustration of Pirouette PLS generated graphs.

For example, the Pirouette® PLS program provides data and graphs to select the appropriate factor by plotting the Predicted Residual Error Sum of Squares (PRESS) versus the factor. See FIG. 5 for Pirouette PLS generated graphs.

TOPNIR is "delivered" as a configured model based on a standard set of software functionality. The well known TOPNIR model relies on a large database of samples that are representative of the production process. TOPNIR has an extensive library of samples that allows the TOPNIR modelers to add samples to the database without all the data having to be provided by the analytical laboratory. Using sophisticated knowledge-based procedures, artificial samples are added to the real samples. This process of densification allows the solution to be tailored uniquely to the production process while requiring a small amount of analytical data. The result is a robust, accurate model that can be extended to meet new process conditions.

Topological modeling allows the updating of the model without the need for manual recalibration to accommodate outliers. This significantly reduces conventional model maintenance and downtime. With a new feedstock or product TOPNIR looks for the closest spectral neighbors in a reference database. The new properties are then calculated as a function of the neighboring characteristics.

Figure 6:
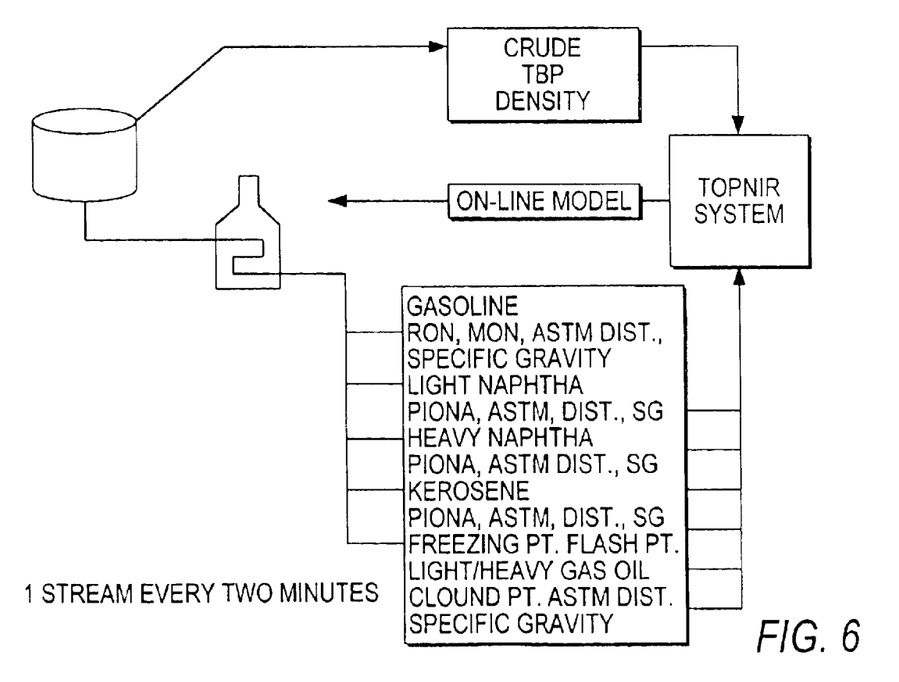
FIG. 6 is an illustration of one aspect of TOPNIR modeling.

Aggregates that relate to specific chemical families, e.g., olefins, are calculated from the spectrum. Spectral planes are used to describe the configured envelope using pairs of aggregates. By selecting the correct aggregates and understanding the product boxes from reference samples, TOPNIR can differentiate between products directly from the spectrum. When a TOPNIR model is developed, a library of reference samples is used to provide poles, such as shown in FIG. 6. The poles are selected to increase the number of samples in the database from the, e.g., 60 samples supplied by the specific production plant to thousands of samples that provide a robust model over the operating envelope of the plant, as in FIGS. 3 and 4 using this densification process.

Figure 7:
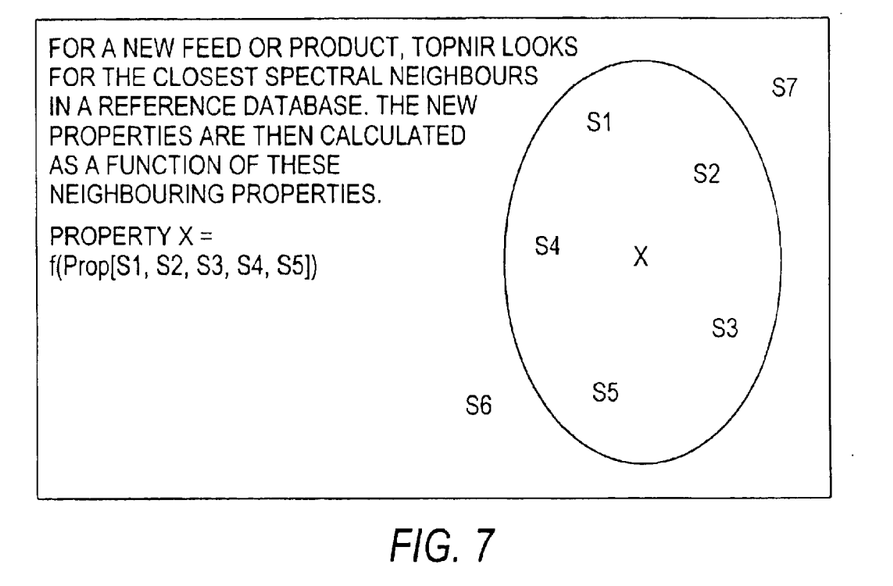
FIG. 7 is an illustration of another aspect of TOPNIR modeling.
Figure 8:
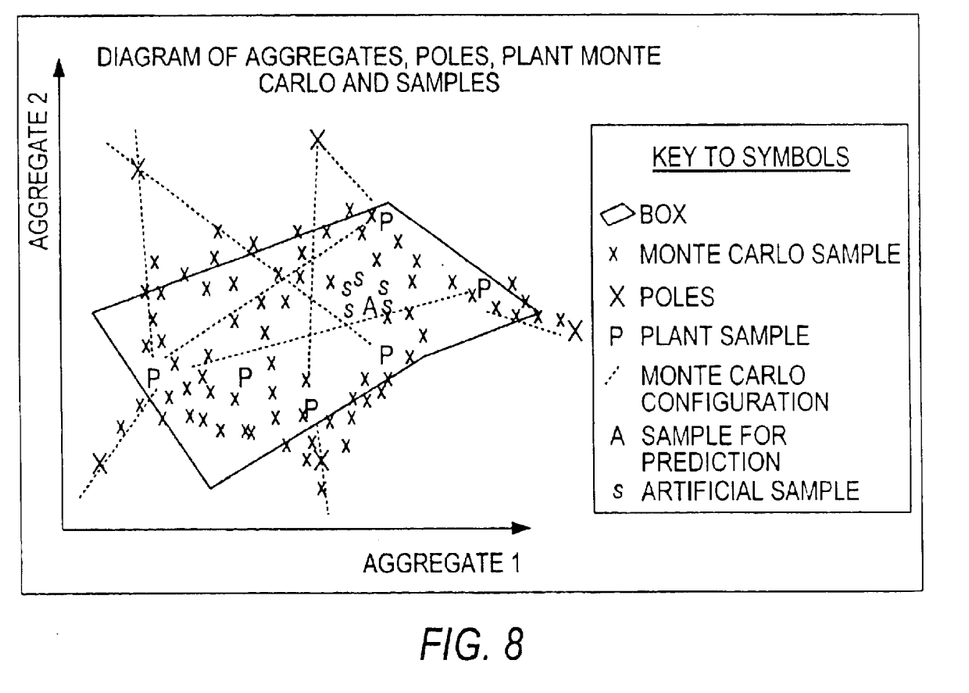
FIG. 8 is an illustration of another aspect of TOPNIR modeling.

Densification is also used during the process of predicting properties. This secondary densification enables the TOPNIR model to cope with outliers. TOPNIR then works by comparing the spectra of the sample with spectra in a reference database. If a match is found, then the properties of the new sample can be predicted from the reference properties of the samples in the database. See FIGS. 7 and 8 for further illustrations of aspects of this well known process.

As the TOPNIR model is based on reference samples and their analytical data, the TOPNIR model can only be guaranteed within the operating envelope. If the operating envelope changes, the spectra will change and the search for neighbors will gradually fail as the operating point leaves the original operating envelope. These changes can be monitored on spectral planes by the position of a sample relative to a box. TOPNIR can cope with multiple process streams operating envelopes.

Model Accuracy

In general, model predictions are accurate as long as the unknown samples are sufficiently similar to the training set samples. Inaccurately predicted samples can be added to the training set to develop a revised model that has greater generality.

Model generality is less of a concern when predicting chemical composition than when predicting physical properties. This is because chemical composition is observed directly as peaks in a sample spectrum. However, the physical properties are inferred from a complicated correlation of their chemical compositions. Model generality is also less of a concern when modeling an individual process unit, for example, a reformer unit of a given refinery, because the composition of the product (for example, reformate) does not vary as widely as do blended gasoline grades.

Even when the unknown samples are too different from the training set to permit accurate/true predictions, NIR predictions can still be quite precise or repeatable. Thus, for controlling or optimizing a process unit, the immediacy and precision of NIR predictions can be more important than their accuracy. This is particularly true when trying to determine changes in process stream properties following a change in operating parameters.

Modeling Process

Figure 9:
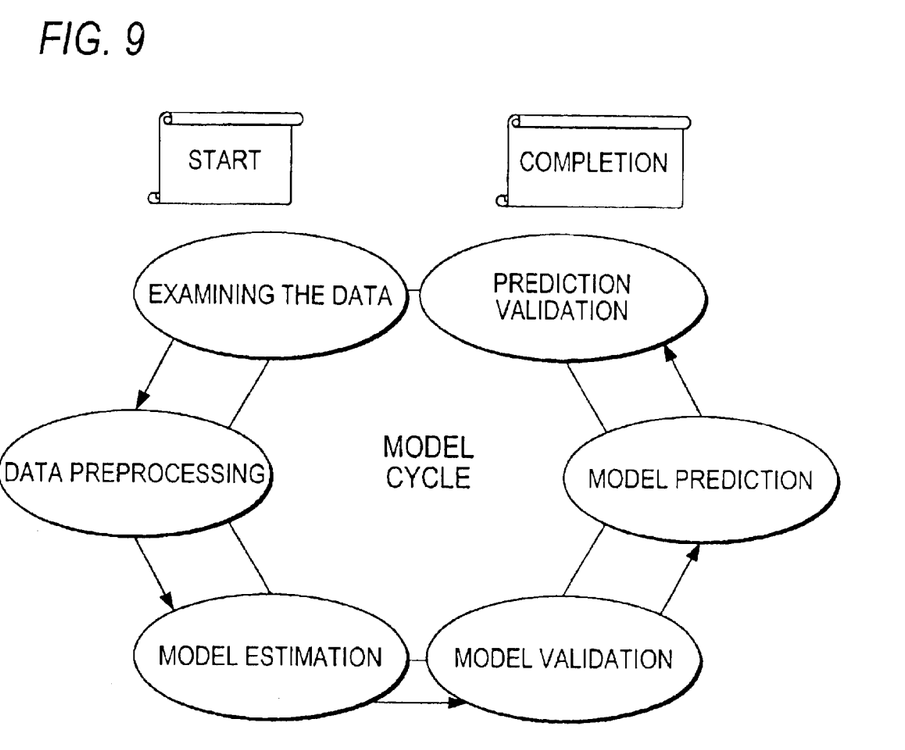
FIG. 9 is an illustration of model maintenance.

To determine if NIR spectroscopy is a reasonable alternative to more traditional methods, many important steps have to be followed and maintained as a recipe for systematic evaluation of the data regardless of the modeling method being used. These steps are considered as the activities required to maintain a model during its life cycle, as shown in FIG. 9:

1. Examining the Data

Once an appropriate data set has been collected, the first step is always to examine the data. This is usually accomplished by examination of plots and/or tables. The primary purpose of this step is to use the human eye to look for obvious errors or features in the data. Because errors can occur in either/both the measurement variables (e.g., spectra) or characteristic values (e.g., concentrations), it is important to examine both of these sets of numbers in this step. The initial review of the data may indicate the need for preprocessing and/or highlight features or samples in the data set that warrant further investigation.

2. Data Preprocessing

When the spectral data plots are presented, one must first determine if there is any baseline drift or slope in the spectra. Baseline subtraction, first derivative and second derivative transformations may be performed to reduce these effects if necessary. There can be random or systematic sources of variation that cause the variation of interest. This unwanted variation might reduce the effectiveness of the model. An understanding of the chemistry or physics underlying these unwanted sources of variation helps with the appropriate selection of processing techniques.

3. Model Estimation

The next step is to generate the Chemometrics model and associated prediction diagnostics. Building a good calibration model is the most important step in NIR analysis. Developing a calibration model involves calculating the regression equation (if it is a PLS model) or topological spectral plans neighbors analyses (if it is a TOPNIR model) based on the NIR spectra and the known analyte information. The model is then used to predict the future unknowns. PLS is the most commonly used linear calibration method, and TOPNIR is most commonly used for nonlinear models.

In developing a PLS calibration model, the parameters evaluated include factors, loadings and scores. On the other hand, the TOPNIR modeling parameters include poles, boxes, spectral planes and the densification process, as will be explained in the experimental procedure section below.

4. Model Validation

The validity of the model must be tested. Usually the way this is done is to split the whole sample set into two sets: one for calibration and the other for validation. If there are not enough samples, "leave-one-out" cross validation can be performed. This means leaving one sample out, using the rest of the samples to build a calibration model and then using the model to predict the one that was left out. The advantage of doing cross validation is that, unlike calibration with a full data set, the sample being predicted is not included in the calibration model. Thus, the model can be tested independently.

5. Model Prediction

Finally, the calibration can be used to predict future unknowns, assuming that the unknowns are in the same sample population as those used in the calibration set. Whether the unknown is an outlier needs to be tested.

6. Prediction Validation

Computer methods rarely fail to produce a prediction result given a model and an unknown. It is therefore important that even apparently reasonable results be validated. Being able to validate prediction results is one of the greatest advantages of using modeling Chemometrics techniques. With the prediction diagnostic tools it is possible to determine when the model is not applicable because of instrument failure or unusual unknown samples. Validation increases the chances of making good decisions based on the outputs of the models by indicating the confidence that should be placed on the predicted values.

As shown in FIG. 9, if the prediction results are not acceptably validated, the procedure returns to the model validation step, or even to an earlier step, to review the model and make whatever changes are necessary.

Thus, PLS and TOPNIR are two different Chemometrics approaches with a common model development life cycle. Each technique has its own advantages and disadvantages. All the known advantages derived from NIR itself are common to both PLS and TOPNIR, such as analysis speed, accuracy of prediction within ASTM accuracy limits, blending process optimization, crude feed characterization etc.

The most widely known PLS disadvantages include the heavy maintenance needed to keep the model operational and updated with the accuracy required, and the large number of samples that are required to enrich the model capability. Also, a separate model has to be constructed for each property, so that for 12 properties predictions, 12 different models have to be constructed. This in turn requires increased work during the models' update.

PLS also has great difficulty in predicting non-linear properties, and has a narrow range of validity if one is trying to predict different sample types (like summer season) that are not covered in the original PLS constructed model.

On the other hand, the TOPNIR model has overcome most of these disadvantages because it can provide multi-property model prediction with a wider prediction range, and shorter time for the model update by including the outliers detected. However, it has been difficult to get both accuracy and robustness in the TOPNIR model. Previously, when the validation set was predicted by both PLS and TOPNIR, the TOPNIR standard error of prediction was higher than the PLS because the TOPNIR database had included all the reported sample results, including some badly mistaken reported lab results.

The TOPNIR modeling tools do not highlight the outliers in a direct way. Usually, all types of mistakes (typo, instrumental, and operator) are enlarged in TOPNIR modeling during the densification process. Thus, if any of these mistakes exist in the TOPNIR database, a larger standard error of prediction is usually reported because of the increased densified mistaken sample population.

However, in accordance with the present invention, the TOPNIR modeling and its densification process become even more powerful by using PLS as a statistical tool in TOPNIR modeling to troubleshoot the outliers in the given data base and, if there are outliers, to reedit the suggested correct measured property values. Thus, the TOPNIR model is updated according to the PLS outlier removal and properties measurements correction. This improved method in accordance with the present invention will be termed PLS-in-TOPNIR herein. In this aspect, the novel PLS-in-TOPNIR method uses PLS for TOPNIR model purification.

In order to compare the results achieved by the conventional TOPNIR method and by the PLS-in TOPNIR method of the present invention, tests were run in accordance with the following protocol.

Instrumentation

The NIR spectrometer used in the tests was the ABB BOMEM MB-Series MB160, which is one of the best performing and most robust analyzer available.

Hardware

Figure 10:
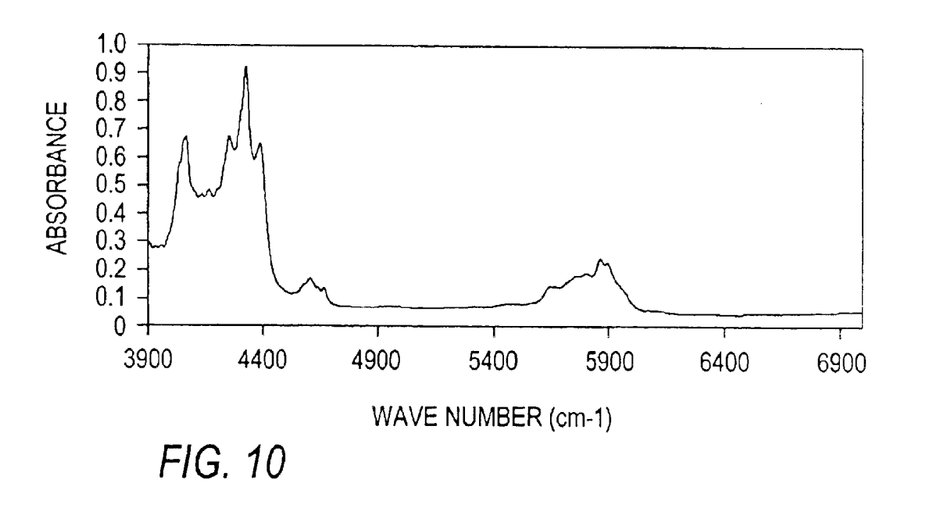
FIG. 10 is an illustration of the full NIR spectrum range.

The hardware consisted of a laser which was the source of the infrared beam, an interferometer, collimators that focused the beam onto the sample and into the detector and a detector that measured the NIR beam after progressing through the sample. The absorption of the NIR beam through the sample across the wavelength range was determined to form the spectrum. Varying degrees of absorption occur dependent on the chemical characteristics of the sample under investigation, thereby providing a fingerprint of the chemical structure of the sample. See FIG. 10 for the full NIR spectrum range.

Software

1. BGrams: A FT-NIR spectrum obtaining tool that is originally provided as a standard package with the ABB BOMEM lab bench analyzer.

2. AIRS: Standard ABB Bomem FT-NIR models prediction media software. All streams and properties PLS models are saved and utilized for unknown samples predictions in this software directory.

3. Pirouette Version 2.7: Comprehensive Chemometrics modeling software used for PLS FT-NIR modeling. It is the ABB Bomem recommended data modeling package.

4. TOPNIR Gasoline Blender: Standard TOPNIR software used to predict the sample stream quality properties using the TOPNIR developed model. Eutech Company provided this version. ABB has purchased the TOPNIR technology.

5. TOPNIR Model Development Package: A special package that covers all the TOPNIR activities and tools required to fully maintain a model (in house) during its life cycle. This includes adding new properties, deleting properties, adding new streams and troubleshooting prediction problems.

Experimental Considerations:

When using an NIR analyzer, instrument characteristics such as sensitivity, resolution and signal-to-noise ratio parameters need to be evaluated. The quality of these values is a function of the light source stability, optics throughput, dispersion/filter element accuracy and detector sensitivity in the instrument. The choice of accessories is application dependent. For liquid samples, transmission and transflectance modes are commonly employed. The path length is sample dependent, usually ranging from 0.1 to 1 cm.

Sample Preparation & Loading

Sample preparation is one of the most crucial steps involved in hydrocarbon (HC) sample analysis. The accuracy and representation of an analysis depend highly on the way the sample is prepared. The temperature of the samples was kept almost constant at room temperature (20±2° C.) during all analyses. Before the hydrocarbon sample was loaded into the sample cell for recording, the NIR spectrum the NIR cell was washed thoroughly with solvents in the following order:

1. Three separate washes, preferably by spectra-grade Toluene. Then the sample cell was dried in air without passing compressed air. It has been found that an in-house compressed air line may introduce some kind of residue from hydrocarbon-based oil which interfaces with NIR spectrum of the sample.

2. Three separate washes of the cell by spectra grade pentane or hexanes were then conducted and the cell was subsequently dried in air.

Finally the sample cell was flushed three times with the sample before a sample was loaded and locked in the cell. During final sample loading process care was taken to avoid locking any air bubbles in the sample.

The AIRS software was used to record customized NIR spectra of samples. This software also would periodically and automatically prompt the operator to calibrate and check any wavelength drift by recording NIR spectrum of spectra grade toluene samples.

Sample Analysis and Data Collection

The interactive software provided with the NIR spectrometer (MB 160) provided menu-driven guidance to the operator from placing the sample cell to collecting the spectral data. In the Fourier-Transform (FT) mode, normally 32 iterations in the chosen NIR spectral range were programmed before an average characteristic spectrum was recorded for a sample. The software automatically and incrementally assigned an NIR spectrum number (for example, AAGXXXX, etc.) of a sample. This software also allowed the operator to record some specific information about the sample, for example, sampling date, time, plant ID, a brief descriptive comment about the sample etc.). For repeatability the NIR spectrum of a sample was collected at different aging times (1–8 weeks after the first spectrum was collected) to assure that the platformate was not degrading on storage. If the successive overlapped spectra showed any significant variation (> than 5%), the properties (RON, etc.) were freshly modeled by TOPNIR and PLSNIR algorithms. The spectrometer would also prompt the operator for a Toluene reference check at every hour interval automatically.

NIR Spectral Modeling:

Once the sample spectrum was collected, its fuel (RON, RVP, etc.) and physical properties (density, distillation cut points, etc.) and compositional characters (paraffinicity, aromaticity, olefinicity, etc.) were predicted either/both by the TOPNIR and PLS-in-TOPNIR models.

The off-line NIR spectrum recording and subsequent modeling typically took 7–10 minutes per sample. However, on-line NIR spectrum recording and modeling would typically take 3–5 minutes per sample from spectrum recording phase to predicting phase. In the on-line monitoring the sample preparation and loading, spectrum recording and model predictions are computer controlled and automatically sequenced. Therefore on-line monitoring has a time advantage as well as an accuracy advantage over off-line analysis.

Results

1. Conventional Methods

A training set of 198 samples was modeled in both PLS (using Pirouette V2.7) and TOPNIR (using TOPNIR Model Development Package) on four selected properties out of 14 properties on a Gasoline stream. The selected properties were the most critical properties needed to operate the MoGas Blender Optimizer System as follows: RON, RVP, Distillation points D-10, and D-50. The five constructed models (four PLS models, one model for each property, and one TOPNIR model for all properties) were validated by predicting 35 new other samples (Validation Set) that were not included in the five models. The obtained predictions were compared to the reference laboratory test results and standard errors of prediction were calculated on each model as shown in Table 1, as shown in FIG. 11.

2. The PLS-in-TOPNIR Method

Then, in accordance with the present invention, PLS was used as a statistical tool in TOPNIR modeling to troubleshoot the outliers in the given data base and to reedit the suggested correct measured property values if there is any. The TOPNIR model was updated according to the PLS outlier removal and properties measurements correction. A new TOPNIR prediction on the validation set was recorded in Table 2, as shown in FIG. 12.

Figure 13:
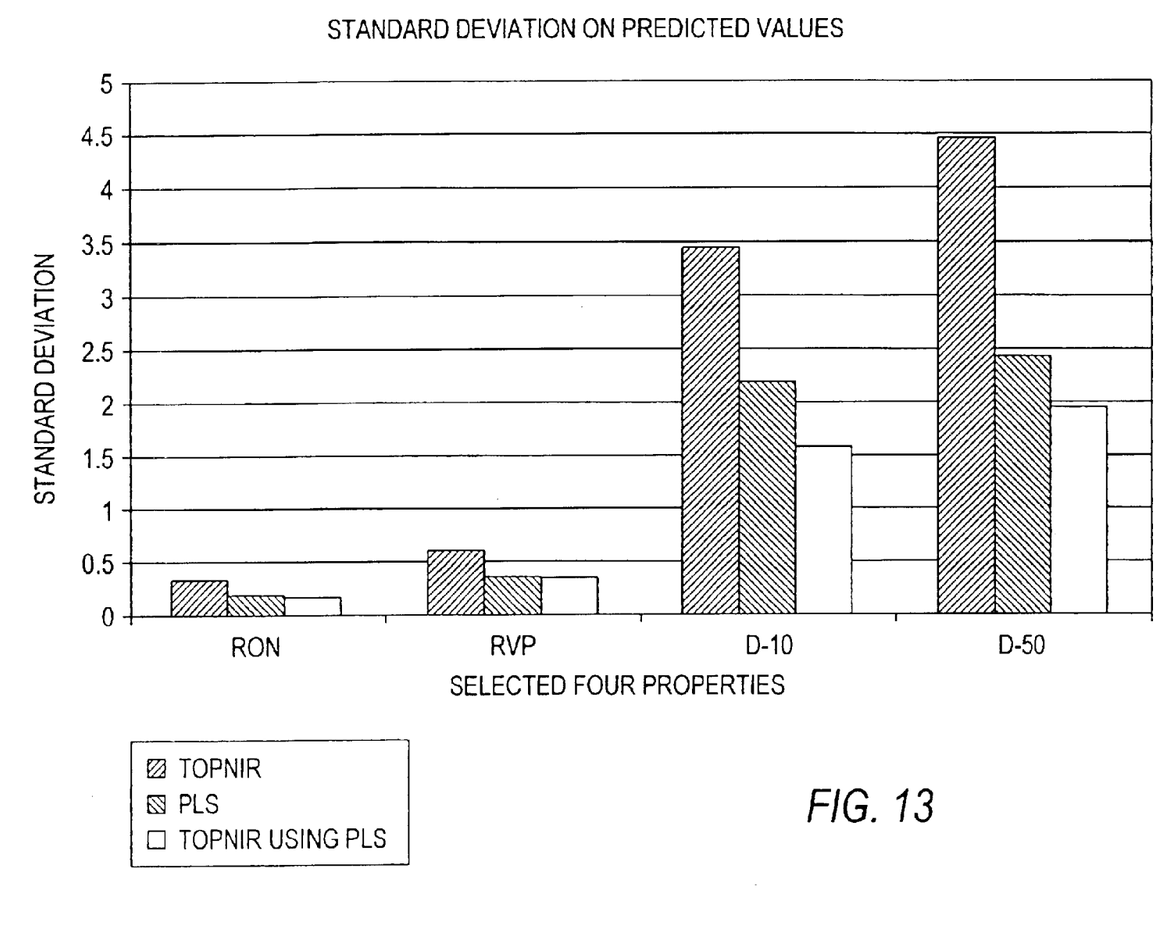
FIG. 13 is a graph of standard deviations of the conventional PLS method, the conventional TOPNIR method and the PLS enhanced TOPNIR method in accordance with the present invention.

The calculated standard errors of predictions on the four measured properties and on the three modeling techniques PLS, TOPNIR and the new PLS-in-TOPNIR are all presented in the graph of FIG. 13.

It will be seen from FIGS. 11–13 that the PLS-in-TOPNIR method in accordance with the present invention provides significantly improved results.

Thus the method in accordance with the present invention integrates the TOPNIR and PLS techniques into one Chemometrics approach. In this method, PLS is used for the first time in treating the TOPNIR database, as follows:

1. PLS is used to highlight the outliers of the TOPNIR database in a systematic order. This result is obtained through the PLS outlier diagnostic curve where all the outliers are ordered according to the size of error. The first worst outlier is chosen by PLS, followed by the second worst outlier and so on. This aspect of PLS in the inventive method may be considered "TOPNIR model purification."

2. As noted above, all types of errors are possible in the delivered lab results for a particular test for a sample (i.e. typo, instrumental and operator errors). As a result, the sample results may be good for most of the tests and bad for one test only for a given sample. In this case the method makes it possible to recorrect the bad test result and avoid wasting the whole set of sample results in the database.

PLS is a strong tool for suggesting an excellent corrected lab test result on the bad given value. This can be achieved by constructing a PLS model for a property, where all outliers have been removed, and predicting all the excluded outliers. The PLS predicted values on the mistaken lab results will then be easily edited out of the TOPNIR database. This PLS function in the method may be considered "TOPNIR model accuracy enhancement."

For example, Table 1 shows the TOPNIR predicted values on a validated set without using PLS to treat the database. In Table 2, all PLS outliers with corrected predictions were edited in the TOPNIR database and the model accuracy (standard errors of predictions) was improved on the measured properties. This aspect may be considered "TOPNIR model accuracy enhancement."

3. The TOPNIR densification process is usually done to increase the number of database samples by adding generic artificial samples. This can be an extra source of error in the model if the database includes badly mistaken samples prior to densification. In the method accordance with the present invention, PLS is used to indicate the wrong densification direction and show where the error is enlarged. All mistaken artificial samples can then be removed from the database and the bad real samples may be reedited with good PLS predicted values.

Thereafter, the densification process can be repeated with an enhanced level of confidence. This step maintains a balanced equation of the model robustness and accuracy.

4. It has also been found that the densification process affected some excellent lab data where bad created neighbors surrounded the good sample. If the bad mistaken values were used in the densification, this greatly affected the model performance. The use of PLS in the method in accordance with the present invention strongly highlights the affected good samples that were turned bad by the misuse of the densification process and prevents the deletion of good samples that should be kept.

The method of the present invention may advantageously be used in the following areas where NIR techniques are valuable.

NIR Refineries Applications:

Crude Distillation Feed and Product Optimization

Variation in crude oil feed to a CDU limits both unit throughput and control of product qualities. Current methods of feed analysis are slow and time-consuming. Measurement of product streams demands intensive analytical equipment with a high maintenance cost. NIR enables crude TBP and rundown streams to be measured on-line in real time, to maximize feed rate to the unit and optimize product quality.

Gasoline and Diesel Blending

The optimization of blending different grades of Gasoline and Gasoil using on-line engines and lab conventional methods can be labor intensive, expensive, slow and of doubtful accuracy. Using NIR along with the DCS blender optimizer system will provide safe on-line blending supported with wide range of properties, speed of analyses, accuracy, and with lower operating cost.

FCC/Hydrocracker Feed and Product Characterization

In many FCC operations the feedstock is not characterized at all. When extreme changes in feedstock are anticipated, an off-line laboratory characterization may be performed. However, this takes at least a day to complete, and continuous unit optimization has not therefore been practical. Using NIR, characterization of FCC feed, and of gasoline and cycle oil products, takes place every two minutes. It is therefore possible with NIR to adopt a feed forward strategy, using the availability of feedstock properties in real time.

Applying an NIR analysis to a particular application requires the development of a reliable calibration model. The most important steps involve a thorough consideration of experimental design and multivariate calibration. Once this is established, one can enjoy the advantages of the NIR analysis. The speed of the analysis will save time and avoid many mistakes instantaneously. The speed advantage is so valuable to engineers involved with on-line process monitoring that instruments are routinely installed in the process line with feedback loops. With NIR, analyzer samples can be analyzed on-the-spot, dramatically reducing costly and time-consuming laboratory analysis.

Integrated use of both PLS and TOPNIR in one package is a completely new Chemometrics approach that should have a great added value in improving the model prediction accuracy. Many other modeling benefits are demonstrated as a result.

I claim:

1. A method of analyzing a substance exhibiting absorption in the near infrared (NIR) region, comprising:

a data obtaining step of obtaining a first data set of NIR spectroscopic data samples by subjecting the substance to NIR spectroscopy;

a generating step of generating a second data set of NIR spectroscopic data samples by processing said first data set using a partial least squares (PLS) regression technique; and an identifying step of identifying a component of the substance by performing a topological near infrared (TOPNIR) analysis on said second data set.

2. The method of claim 1, wherein said generating step includes the steps of:

identifying outliers in said first data set; and determining a respective PLS regression error for each of the identified outliers.

3. The method of claim 2, wherein said generating step further includes the step of ordering the identified outliers in accordance with the respective PLS regression errors.

4. The method of claim 3, wherein said generating step further includes the step of setting said second data set to be said first data set without any of the identified outliers having a respective PLS regression error greater than a specified value in accordance with said ordering step.

5. The method of claim 3, wherein said generating step further includes the step of setting said second data set to be said first data set with a corrected value for any of the identified outliers having a respective PLS regression error greater than a specified value in accordance with said ordering step.

6. The method of claim 2, wherein said generating step further includes the step of setting said second data set to be said first data set without any of the identified outliers having a respective PLS regression error greater than a specified value.

7. The method of claim 2, wherein said generating step further includes the step of setting said second data set to be said first data set with a corrected value for any of the identified outliers having a respective PLS regression error greater than a specified value.

8. The method of claim 1, wherein said generating step includes the steps of:

predicting a corrected test result for a bad data sample in said first data set using a PLS regression technique; and substituting the corrected test result for the bad data sample.

9. The method of claim 8, wherein said predicting step includes the steps of:

identifying outliers in said first data set as bad data samples;

constructing a PLS regression model for a property of the component based on said first data set with the outliers excluded;

generating a corrected test result for each bad data sample by predicting values for the excluded outliers based on the PLS regression model.

10. The method of claim 1, wherein the substance to be analyzed is a petroleum refinery product.

11. A method of analyzing a substance exhibiting absorption in the near infrared (NIR) region, comprising:

a data obtaining step of obtaining a first data set of real NIR spectroscopic data samples by subjecting the substance to NIR spectroscopy;

an analysis step of performing a first topological near infrared (TOPNIR) analysis on said first data set to generate a second data set of NIR spectroscopic data samples;

a generating step of generating a third data set of NIR spectroscopic data samples by processing said second data set using a partial least squares (PLS) regression technique; and an identifying step of identifying a component of the substance by performing a second TOPNIR analysis on said third data set.

12. The method of claim 11, wherein said analysis step includes the step of TOPNIR densification of said first data set to generate said second data set as including the real data samples of said first data set and at least one artificial data sample.

13. The method of claim 12, wherein said generating step includes the step of using said PLS regression technique to identify a wrong densification direction of said TOPNIR densification.

14. The method of claim 13, wherein said generating step includes the step of TOPNIR densification of said second data set with a corrected densification direction based upon the identified wrong densification direction to generate said third data set.

15. The method of claim 12, wherein said generating step includes the steps of:

predicting a corrected test result for a bad data sample in said first data set using said PLS regression technique; and substituting the corrected test result for the bad data sample to generate said third data set.

16. The method of claim 15, wherein said generating step includes the step of TOPNIR densification of said second data set to generate said third data set.

17. The method of claim 16, wherein said generating step includes the steps of:

using said PLS regression technique to identify a good one of the real data samples that has been affected by said TOPNIR densification to appear to be a bad data sample; and including the identified one real data sample in said second data set.

18. The method of claim 12, wherein said generating step includes the steps of:

identifying a good one of the real data samples that has been affected by said TOPNIR densification to appear to be a bad data sample; and including the identified one real data sample in said second data set.

19. The method of claim 11, wherein the substance to be analyzed is a petroleum refinery product.

* * * * *